United States Patent [19]

Neve

[11] Patent Number: 5,672,805
[45] Date of Patent: Sep. 30, 1997

[54] TRANSGENIC MICE EXPRESSING THE NEUROTOXIC C-TERMINUS OF β-AMYLOID PRECURSOR PROTEIN

[75] Inventor: Rachael L. Neve, Irvine, Calif.

[73] Assignee: The Regents of the University of California, Oakland, Calif.

[21] Appl. No.: 732,404

[22] Filed: Jul. 18, 1991

[51] Int. Cl.$^6$ .............. C12N 5/00; C12N 15/00; A61K 49/00

[52] U.S. Cl. .............. 800/2; 800/DIG. 1; 424/9.2; 935/62

[58] Field of Search .............. 800/2, DIG. 1; 514/44; 424/9.2; 935/62

[56] References Cited

FOREIGN PATENT DOCUMENTS

| 0451700A1 | 10/1991 | European Pat. Off. |
| 34794 | 8/1988 | Japan . |
| WO8906689 | 7/1989 | WIPO . |
| WO9005138 | 5/1990 | WIPO . |
| WO9014840 | 12/1990 | WIPO . |
| WO9119810 | 12/1991 | WIPO . |
| WO9206187 | 4/1992 | WIPO . |

OTHER PUBLICATIONS

Wirak, et al., *Science*, 253:323–325 (1991).
Sandhut, et al., *The Journal of Biological Chemistry*, 266:21331–21334 (1991).
Selkoe, *Science*, 354, 432–433 (1991).
Marx, *Science*, 253, 266–267 (1991).
Cork, et al., Animal Models of Degenerative Neurological Disease, in Animal Models: Assessing the Scope of Their Use in Biomedical Research, pp. 241–269 (1987) Alan R. Liss, Inc.
Dyrks, et al., EMBO J. 7, 949 (1988).
Kang, et al., Nature 325, 733 (1987).
Goldgabar, et al., Science 235, 877 (1987).
Tanzi, et al., Science 235, 880 (1987).
Robakis, et al., Proc. Natl. Acad. Sci. USA 84, 4190 (1987).
Ponte, et al., Nature 331, 525 (1988).
Kitaguchi, et al., Nature 331, 530 (1988).
Glenner, et al., Biochem. Biophys. Res. Commun. 120, 885 (1984).
Glenner, et al., Biochem. Biophys. Res. Commun. 122, 1131 (1984).
Masters, et al., Proc. Natl. Acad. Sci. USA 82, 4245 (1985).
Esch, et al., Science 248, 1122 (1990).
Yankner, et al., (1989) Science 245, 417.
Wolf, et al., EMBO J. 9, 2079 (1990).
Maruyama, et al., Nature 347, 566 (1990).
Neve, et al., Neuron 5, 329 (1990).
Boyce, F.M., et al., PNAS 88:1276 (1991).

*Primary Examiner*—Deborah Crouch
*Attorney, Agent, or Firm*—Walter H. Dreger; Jan P. Brunelle

[57] ABSTRACT

The present invention provides non-human, transgenic animals for use as a model for the study of Alzheimer's Disease. The animals exhibit pathology associated with Alzheimer's Disease. The phenotype is conferred in the animals by the introduction of an amyloid-containing polypeptide fragment of amyloid precursor protein, through the introduction of the DNA into the germ and somatic cells of the animal by transgenic methods.

8 Claims, 9 Drawing Sheets

```
                                    AGATCTCTGAAGTGAAGATGGATGCAGAATTC  1800
                                     I  S  E  V  K  M  D  A  E  F
CGACATGACTCAGGATATGAAGTTCATCATCAAAAATTGGTGTTCTTTGCAGAAGATGTG        1860
 R  H  D  S  G  Y  E  V  H  H  Q  K  L  V  F  F  A  E  D  V
GGTTCAAACAAAGGTGCAATCATTGGACTCATGGTGGGCGGTGTTGTCATAGCGACAGTG        1920
 G  S  N  K  G  A  I  I  G  L  M  V  G  G  V  V  I  A  T  V
ATCGTCATCACCTTGGTGATGCTGAAGAAGAAACAGTACACATCCATTCATCATGGTGTG        1980
 I  V  I  T  L  V  M  L  K  K  K  Q  Y  T  S  I  H  H  G  V
GTGGAGGTTGACGCCGCTGTCACCCCAGAGGAGCGCCACCTGTCCAAGATGCAGCAGAAC        2040
 V  E  V  D  A  A  V  T  P  E  E  R  H  L  S  K  M  Q  Q  N
GGCTACGAAAATCCAACCTACAAGTTCTTTGAGCAGATGCAGAACTAGACCCCCGCCACA        2100
 G  Y  E  N  P  T  Y  K  F  F  E  Q  M  Q  N
GCAGCCTCTGAAGTTGGACAGCAAAACCATTGCTTCACTACCCATCGGTGTCCATTTATA        2160

GAATAATGTGGGAAGAAACAAACCCGTTTTATGATTTACTCATTATCGCCTTTTGACAGC        2220

TGTGCTGTAACACAAGTAGATGCCTGAACTTGAATTAATCCACACATCAGTAATGTATTC        2280

TATCTCTCTTTACATTTTGGTCTCTATACTACATTATTAATGGGTTTTGTGTACTGTAAA        2340

GAATTTAGCTGTATCAAACTAGTGCATGAATAGATTCTCTCCTGATTATTTATCACATAG        2400

CCCCTTAGCCAGTTGTATATTATTCTTGTGGTTTGTGACCCAATTAAGTCCTACTTTACA        2460

TATGCTTTAAGAATCGATGGGGGATGCTTCATGTGAACGTGGGAGTTCAGCTGCTTCTCT        2520

TGCCTAAGTATTCCTTTCCTGATCACTATGCATTTTAAAGTTAAACATTTTAAGTATTT         2580

CAGATGCTTTAGAGAGATTTTTTTTCCATGACTGCATTTTACTGTACAGATTGCTGCTTC       2640

TGCTATATTTGTGATATAGGAATTAAGAGGATACACACGTTTGTTTCTTCGTGCCTGTTT       2700

TATGTGCACACATTAGGCATTGAGACTTCAAGCTTTTCTTTTTTTGTCCACGTATCTTTG       2760

GGTCTTTGATAAAGAAAAGAATCCCTGTTCATTGTAAGCACTTTTACGGGGCGGGTGGGG      2820

AGGGGTGCTCTGCTGGTCTTCAATTACCAAGAATTCTCCAAAACAATTTTCTGCAGGATG      2880

ATTGTACAGAATCATTGCTTATGACATGATCGCTTTCTACACTGTATTACATAAATAAAT      2940

TAAATAAAATAACCCCGGG
```

FIG._10

TRANSGENIC MICE EXPRESSING THE NEUROTOXIC C-TERMINUS OF β-AMYLOID PRECURSOR PROTEIN

ACKNOWLEDGMENT

This invention was made with certain United States government support in the form of grants from the National Institute of Health. The United States has certain rights in this invention.

Reference is made to the patent application filed concurrently, Attorney Docket No. A-54443. That application refers to animals useful as models for Alzheimer's Disease made by transplanting cells into the brains of the animals.

FIELD OF THE INVENTION

The present invention in all of its associated aspects is directed to transgenic non-human animals whose brains express amyloid-containing polypeptide fragments of APP, and to methods of producing and using such animals. The novel animal models of the present invention thus create means to test and evaluate new drugs and treatments of Alzheimer's Disease.

BACKGROUND OF THE INVENTION

For convenience of the reader, the references referred to in the text are listed numerically in parentheses. These numbers correspond to the numerical references listed in the appended bibliography. By these references, they are hereby expressly incorporated by reference herein.

Alzheimer's Disease is a human progressive neurodegenerative disorder which occurs in middle and late life and is characterized by gradual loss of memory, reasoning, orientation and judgment. It is the most frequent cause of dementia and presently affects over two million older Americans. One of the problems associated with the study of Alzheimer's Disease is the lack of good animal models, since animals such as mice and rats do not manifest the symptoms of Alzheimer's Disease. Currently, rhesus monkeys older than 23 years of age are one of the only available models in which to study Alzheimer's Disease. See (1). Thus given the state of the art, it is apparent that a need exists for animal model systems to study Alzheimer's Disease and its effects.

Characteristic of brain tissue of individuals suffering from Alzheimer's Disease are alterations in the immunostaining patterns of the monoclonal antibody Alz-50. (2). Alz-50 selectively immunodetects a modified form of the microtubule associated protein called tau present in the Alzheimer's disease brain. (2), (3). The immunoreactivity of Alz-50 shifts from the axonal to the somatodendritic domain of neurons in the cortex; this axonal disruption and the dislocation of tau protein from its usual axonal domain into neuronal cell bodies and dendrites characterize the pathology of Alzheimer's Disease (4).

Also indicative of the Alzheimer's Disease brain is a disruption of the immunoreactivity of the F5 antibody, which recognizes the nine carboxyterminal amino acids of amyloid precursor protein (hereinafter APP). This antibody normally immunoreacts with both pyramidal cell bodies and neuropil in a normal human cortex and hippocampus (5). In the Alzheimer's Disease brain, the F5 antibody displays dramatically decreased cell body staining in the hippocampus, and instead appears as punctate accumulations in secondary lysosomes and in the neuropil (5).

A further hallmark of Alzheimer's Disease pathology is the deposition of amyloid in neuritic plaques and along the walls of the cerebral vasculature (6), (7). Amyloid deposition occurs in three locations: intracellularly associated with neurofibrillary tangles in the cortex, extracellular amyloid deposits called neuritic plaques, and as extracellular cerebrovascular amyloid in the walls of meningeal and intracortical vessels (8). The principle component of amyloid in humans is a 4-kilodalton protein, also called beta/A4, that is believed to be derived from one or more of four identified precursor proteins with predicted lengths of 695, 751, 770, and 714 amino acids, respectively (9–16). Another β-amyloid related sequence lacking identity with the Kang et al. (9) sequence is reported in published patent application WO 90/14840. Amyloid is believed to span about 28 to 42 amino acids, although its precise length is unknown (17–19). The deduced sequences of these APPs, which are translated from alternatively spliced mRNAs transcribed from a single gene, suggest that they are glycosylated, membrane spanning proteins, containing both transmembrane and cytoplasmic domains (9–12). Other animals such as rats, mice, dogs and primates also have homologous APP sequences within their genomes, with corresponding homology to the amyloid encoding region (20–22).

Recent evidence indicates that normal processing of APP is a membrane associated event that occurs within the extracellular domain of amyloid (23). Hence, the generation of amyloid in Alzheimer's Disease appears to be the result of an abnormal cleavage or other post-translational event; however, the molecular mechanisms of amyloidogenesis remain unclear. Also uncertain is the role of amyloidogenesis in the development of Alzheimer's Disease pathology.

The carboxyterminal APP fragment (APP-C104, comprising the C-terminal 104 amino acids of APP; previously referred to as APP-C105 or AB-1) has been shown to be neurotoxic, causing transfected cells which express the fragment to degenerate when induced to differentiate into neuronal cells with nerve growth factor (24). Additionally, conditioned media from these cells is toxic specifically to neurons in primary rat hippocampal cultures (24). This toxicity can be removed from the medium by immunoabsorbtion with an antibody to the fragment which suggests that this fragment is secreted by the transfected cells and is neurotoxic.

One problem in the investigation of the role of amyloid or amyloid containing polypeptides in Alzheimer's Disease pathology is that these shortened peptides that comprise the amyloid protein and the C-terminal cytoplasmic domain of APP have a strong tendency to self-aggregate and are resistant to solubilization in physiological solutions, and thus are difficult to handle (8, 25–27). Moreover, the expression of this carboxyterminal APP fragment in primate cultured cells has been shown to lead to the production of a 16 kilodalton protein that aggregates and accumulates into deposit-like structures and also results in the formation of amyloid-like fibrils (28, 29). However, this aggregation of amyloid is completely intracellular. Thus, direct injection of the APP-C105 protein to study the deposition of amyloid within the brain is difficult and the results are hard to interpret.

Also of interest is the recent finding that a specific spliced form of the APP gene, which does not contain the amyloid encoding region, is elevated in the nucleus basalis, occipitotemporal cortex, and parahippocampal gyrus in Alzheimer's Disease brains, relative to controls (30).

Similarly, there is an apparent lack of correlation between amyloid deposition in the brain and the loss of cognitive functions in individuals with Alzheimer's Disease (31–33).

These two findings taken together suggest that amyloid deposition is but one of the factors contributing to the pathology and symptoms of Alzheimer's Disease. This erodes the current consensus that amyloid is a quintessential component involved in the manifestations of Alzheimer's Disease.

The transplantation of cells that express an amyloid-containing polypeptide fragment of APP into the brains of non-human animals results in the development of pathology associated with Alzheimer's Disease in the brains of said animals. PC12 cells that express the polypeptide APP-C105 result in several alterations of normal brain histology such as: immunostaining with Alz-50, a monoclonal antibody that recognizes an Alzheimer's Disease modified form of the protein tau; gross neuronal loss and disruption of the neuropil in the hippocampus of the animals. However, there is a surprising lack of amyloid deposition present in these animals containing the transplants.

SUMMARY OF THE INVENTION

The present invention is based on the determination that expressed fragments of APP containing the amyloid protein are implicated in pathology associated with Alzheimer's Disease. From that finding, the present invention provides non-human transgenic animals that can serve as models for screening materials that could have an effect on said pathology, and therefore, prove clinically useful for the prophylactic or therapeutic treatment of Alzheimer's Disease and/or its symptoms.

The present invention is based on the further finding that animals exhibiting the pathology associated with Alzheimer's Disease may be produced by expressing an amyloid-containing polypeptide fragment of an APP in the brain of said animals. This pathology is comprised not only of amyloid deposition, surprisingly, but also of other manifestations of Alzheimer's Disease: gross neuronal loss, disorganization of certain regions of the hippocampus, and immunostaining alterations usually found in individuals with Alzheimer's Disease.

The invention may be realized by through the use of transgenic techniques, resulting in animals whose germ and somatic cells contain the polypeptide encoding region which is expressed as a specific phenotype. The invention is thus directed towards such transgenic animals and to all associated equivalents.

In one aspect, the invention provides non-human, transgenic animals whose brains express an amyloid-containing polypeptide fragment of an APP. Suitable polypeptide fragments for the production of these animals contain the amyloid protein region.

With respect to the class of acceptable polypeptides for introduction into these animals, the polypeptide fragment may also be neurotoxic.

Also suitable for the class of acceptable polypeptides are those that are homologous to the human APP-695 polypeptide fragment APP-C104 but originating in the genome of some other animal.

Also acceptable as a polypeptide fragment for the production of these animals is the human APP-695 polypeptide fragment, APP-C104, itself.

In a second aspect, the present invention involves the method of using the described animals as a model for pathology associated with Alzheimer's Disease by monitoring the effects of experimental factors on this pathology. These experimental factors may be drugs, hormones, polypeptides or nucleotides, or combinations thereof. The composition of the experimental factor to be tested may contain other components as needed in amounts suitable for effective experimentation. Furthermore, the invention encompasses monitoring the effects of these experimental factors by measuring the inhibitory effects of the factors on the development or expression of the pathology associated with Alzheimer's Disease. In this way materials may be tested for the treatment of Alzheimer's Disease or to test whether they confer protection against the development of the pathology of Alzheimer's Disease or therapeutic value.

DETAILED DESCRIPTION OF THE INVENTION

Description of the Preferred Embodiment

Applicants have found that amyloid-containing polypeptide fragments of APP produce brain pathology associated with Alzheimer's Disease when expressed in the brains of mice. The present invention is illustrated by means of a model non-human transgenic animal system whereby the brains of said animals express an amyloid-containing polypeptide fragment, APP-C104, of the human amyloid precursor protein APP-695. The animal may be made by utilizing transgenic methodology to introduce the DNA encoding said polypeptide into the germ and somatic cells of said animal.

Furthermore, the use of a so-called brain specific promoter to allow expression of the polypeptide fragment solely within the brain may also be used.

In a preferred embodiment, the promoter to be utilized is the dystrophin neural promoter, described in (34). The dystrophin protein is made from two separate promoters; one enables transcription in muscle tissue, and the other "neural" promoter enables much smaller amounts to be made within the brain. The promoter is ideal for several reasons: it allows expression in virtually all neurons, and it is expressed at extremely low levels in individual neurons, allowing gradual neurodegeneration rather than massive brain death. However, the two promoters appear to show tissue selectivity rather than strict specifities, since small amounts of the brain transcript have been found in muscle tissue, and vice versa.

It follows from the results herein that a variety of APP C-terminal fragments of different lengths that contain the amyloid protein sequence will find use in the present invention. For example, C-terminal fragments that are less than about 104 amino acids but contain the amyloid-encoding functionality would be expected to produce the same or similar results. Similarly, C-terminal fragments that are greater than about 104 amino acids and include the amyloid-encoding functionality are also covered by the present invention. Additionally, fragments that contain protein sequences that flank the amyloid protein sequence on either side, i.e. upstream or downstream of the amyloid protein sequence, are also included within the ambit of the invention.

The "non-human animals" of the invention comprise any non-human transgenic animal whose brain expresses an amyloid-containing polypeptide fragment of an APP. Such non-human animals include vertebrates; preferred non-human animals are selected from the rodent family. The mouse was selected as the preferred experimental model herein.

Having described the particular model system employed in the present research for the creation of animals whose brains express an amyloid-containing polypeptide fragment of an APP, and showing that these animals exhibit the pathology associated with Alzheimer's Disease, and detailing how these animals can be produced and used to test materials to treat and protect against the pathology associated with Alzheimer's Disease, the present disclosure is sufficient to enable one skilled in the art to use this knowledge to produce the end results by equivalent means using generally available techniques.

Starting materials are readily available or may be derived from readily available starting materials without undue experimentation.

Generally available and well known in the art are techniques enabling the introduction of DNA into the germ and somatic cells of non-human animals (35).

Furthermore, the methods for evaluating the presence of said DNA to determine the success of the techniques are also readily available and well known in the art, through the use, for example, of either the hybridization of DNA probes to determine the presence of the exogenous DNA, or by the appearance of pathology associated with Alzheimer's Disease. A successful reproduction of the present invention will result in animals that exhibit the pathology associated with Alzheimer's Disease, and whose offspring likewise exhibit said pathology.

BRIEF DESCRIPTION OF THE DRAWINGS

FIGS. 4(A–E): E1-42 immunoreactivity in Ammon's horn of the hippocampus of a transgenic animal (A), compared with that of a control animal (B). While low level staining of cell bodies in the pyramidal cell layer and in additional scattered cells is seen in the control mouse, darker punctate accumulations of E1-42 immunoreactivity throughout the hippocampus are unique to the transgenic mice. Higher magnifications of the punctate intracellular deposits of E1-42 immunoreactivity in transgenic animals are shown in panels C–E. The scale bars in A–C represent 100 um; the bars in D and E represent 10 um.

FIGS. 5(A–B): E1-42 immunoreactivity in the hilus of a transgenic animal. This region of the hippocampus possessed the highest density of cells with intracellular amyloid deposits (A); punctate deposits are also visible in the neuropil (B). An enlargement of the field outlined in (A) is depicted in (B). The scale bar in both panels represents 100 um.

FIGS. 6(A–C): E1-42 immunoreactivity in the neuropil at the CA2/3 boundary in transgenic animals with a high copy number of the transgene. Punctate β/A4 deposits have virtually disappeared from cell bodies of this region in these mice, and are instead found accumulated in curly dystrophic-appearing fibers throughout the area (A). A greater magnification of a sector of the region displayed in (A) is shown in (B). E1-42 immunostaining of a control animal in shown in (C) for comparison. (A) and (C) are the same magnification (scale bar represents 100 um); the scale bar in (B) represents 10 um.

FIGS. 7(A–F): F5 immunostaining of a transgenic (A–C) and a control (D–F) animal at the CA2/3 boundary in the hippocampus. Note that the F5 epitope (the carboxyterminus of APP) has accumulated in punctate vesicular structures within the cell somata, and has become dislocated to the neuropil in the transgenic animal. (A–C) and (D–F) show increasing magnifications of the same region in each animal. Scale bars in A, B, D and E represent 100 um; bars in C and F represent 10 um.

FIGS. 8(A–D): F5 immunostaining of the pyramidal cell layer at the CA2/3 boundary in the hippocampus of an Alzheimer's disease (7A) and a control (7B) individual, illustrating the shift of F5 immunoreactivity to punctate accumulations in the cell body and neuropil in the Alzheimer's disease hippocampus relative to the control. Note that the density of pyramidal cells in this region is less in the aged human brain than it is in mice. (C) and (D) are high powered depictions of the accumulation of F5 epitope in vesicular structures in the cell body in the brains of a transgenic animal and an Alzheimer's Disease individual, respectively. Scale bars in A and B represent 100 um; bars in C and D represent 10 um.

FIGS. 9(A–B): Thioflavin S fluorescence around blood vessels in the hippocampus of a transgenic mouse from line 2. (A) and (B) show different magnifications of the fluorescence. No thioflavin S fluorescence was visible in control mice. The scale bar in A represents 100 um; the scale bar in B represents 10 um.

DEFINITIONS

By the term "amyloid protein" or grammatical equivalents, herein is meant a form of the amyloid or beta/A4 protein. Since the exact length of amyloid is uncertain presently, and indeed may vary, the definition is meant to include that portion of the amyloid protein which, when used in accord with the present invention, will result in the development of pathology associated with Alzheimer's Disease in the host animal. For example, the term includes the 28 to 43 amino acid fragment that comprises a principal component of amyloid plaques in Alzheimer's Disease.

By the term "amyloid-containing polypeptide fragment of APP", or grammatical equivalents, herein is meant any portion of an APP, whether from any one of the human APPs characterized so far in the literature, or from another animal whose class of APPs shows homology to the human class of APPs. Furthermore, this polypeptide fragment would contain a form of the amyloid or beta/A4 protein, a length of about 28 to 42 amino acids that is functional for purposes hereof, for example. As noted above, "amyloid protein" has a functional definition, directly relating to its utility in resulting in pathology associated with Alzheimer's Disease. Thus, it is necessary that the "fragment" contains all or a functional portion of the amyloid sequence. Other polypeptide sequences flanking such a functional amyloid sequence may be present so long as the functionality of the functional amyloid sequence is not compromised. In further preferred embodiments, this fragment is either the human APP-695 polypeptide fragment APP-C104 or a fragment homologous to it but originating from a different animal genome.

By the term "all or part of the amyloid sequence" is herein meant that portion of the amyloid protein which, when incorporated into the present invention, will result in the development of pathology associated with Alzheimer's Disease. Since the exact length of amyloid is uncertain, and indeed may vary, an exact definition of the length of the amyloid protein necessarily relies on the functionality, i.e. the ability to generate pathology associated with Alzheimer's Disease in the host animal when incorporated into the cells thereof in accord with the present invention. Further encompassed by the term "amyloid protein" are those sequences that show homology to the human amyloid but originate from a different animal genome.

By the term "pathology associated with Alzheimer's Disease" herein is meant the appearance of any one of a number of physical or chemical abnormalities existing in individuals with Alzheimer's Disease. Such abnormalities may include, but are not limited to, the deposition of amyloid or amyloid fibrils; a loss of neurons or gross neurodegeneration; shrinkage of the cortex; alterations in the immunostaining of the monoclonal antibody Alz-50, which recognizes as its antigen a modified form of the microtubule associated protein tau; or accumulation of fragments of APP in lysosomes and in the neuropil.

By the term "experimental factors" or grammatical equivalents, herein is meant any material or substance, known or yet to be discovered, that may be tested for its effects on the pathology associated with Alzheimer's Disease. These factors may have no previous relationship to the treatment of Alzheimer's Disease, or may be implicated by prior research as effecting the symptoms and pathology associated with Alzheimer's Disease. These factors may be selected, by way of example only, from the group consisting of known or yet to be defined or discovered drugs, hormones, polypeptides or nucleotides.

By the term "brain specific promoter" or its grammatical equivalents is herein meant a DNA promoter that is activated preferentially within cells of the brain. A DNA promoter is required for the transcription of DNA into RNA, and brain specific promoters preferentially allow transcription within the brain. This results in the expression of the protein of interest, here, an amyloid-containing polypeptide fragment of APP, predominantly within the brain of the transgenic animal and results in little or no translation within any other germ or somatic cells. In a preferred embodiment, the dystrophin neural promoter is used, which has a high specificity for brain tissue expression.

One skilled in the art may utilize the present invention to test compounds for efficacy against the symptoms and pathology of Alzheimer's Disease, as well as efficacy for protection against the development of the disease. These compounds will be formulated in accord with known techniques to produce useful pharmaceutical compositions that are pharmaceutically acceptable for appropriate administration in the treatment or prevention of Alzheimer's Disease. Such compounds will be tested for safety, dose response and efficacy in humans as per federal regulations. Ordinary studies conducted pursuant to those regulations will determine the safety and efficacious dose regimens appropriate in the circumstances for the treatment of Alzheimer's Disease. These compounds could be administered to patients with Alzheimer's Disease via standard formulations such as topical, oral, parenteral, or rectal formulations, alone or in combination with each other or other compounds needed for efficacious treatment, for example, compounds needed to cross the blood-brain barrier. The compounds may be administered at regular intervals or as a single bolus, or as a continuous infusion.

Furthermore, the screening procedures to determine the presence of pathology associated with Alzheimer's Disease, including the histological examination of brain tissues, immunochemical evaluation of antibodies such as Alz-50 and F5 that are useful in the evaluation of Alzheimer's Disease, and thioflavin S staining for the presence of extracellular amyloid deposits are documented in the literature. It is further envisioned that evaluations of compounds tested for efficacious treatment or prevention of Alzheimer's Disease may be done using assays or procedures not utilizing the examination of brain tissues. Such tests could include behavioral evaluations of animals undergoing treatment with the compounds.

EXAMPLE

Production of Transgenic Mice

Figure 1:
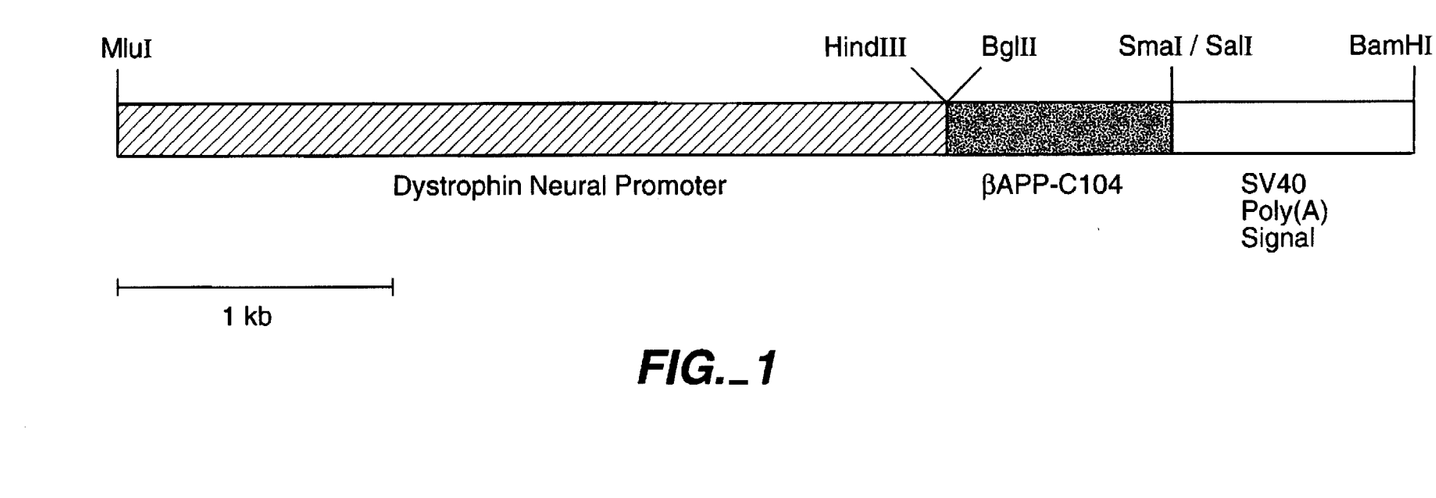
FIG. 1: Schematic drawing of the dystrophin brain promoter βAPP-C104 fusion transgene.
Figure 10:
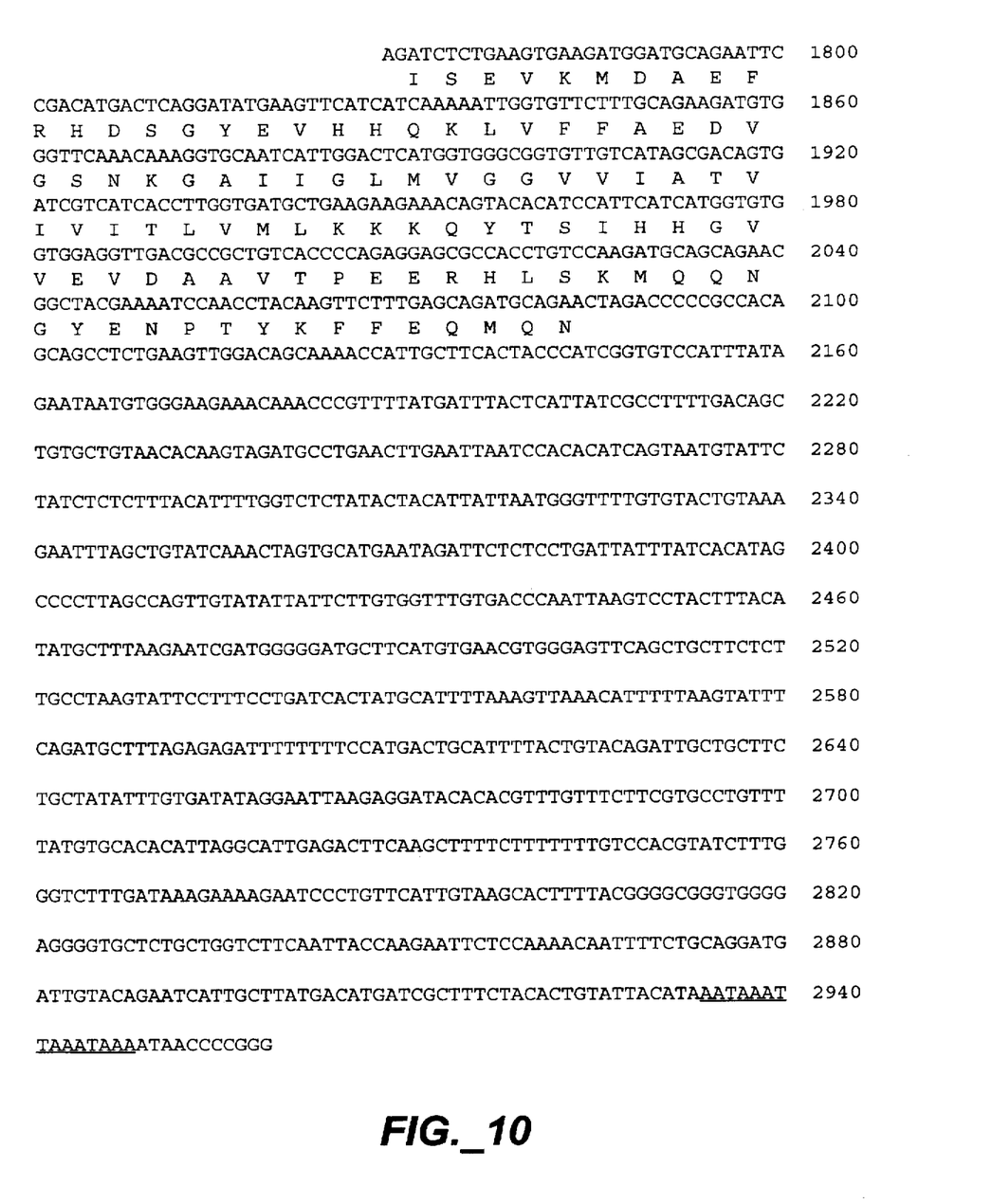

The BglII-SmaI fragment of the βAPP-695 cDNA (basepairs 1769 to 2959 according to the sequence of Kang et al. (9)) (see FIG. 10) was cloned into a modified form of pRSV β-globin (36) in which the β-globin coding sequence had been replaced with a polylinker. The RSV promoter was replaced with the dystrophin neural promoter (34) by subcloning the latter (a three kilobase HindIII fragment) into MluI-HindIII digested PRSVβAPP-C105 in which the MluI cohesive end had been filled in and ligated with HindIII linkers which were designed to retain the MluI site. The APP-C104 transgene, together with the upstream dystrophin promoter and the downstream SV40 splice and polyadenylation sequences, was excised from plasmid sequences by digestion with MluI and BamHI. See FIG. 1. The DNA fragments were separated by agarose gel electrophoresis, and the transgene DNA fragment was electroeluted and ethanol precipitated. DNA concentration was determined by $OD_{260}$ absorbance. DNA was microinjected into the pronuclei of fertilized eggs from F2 hybrid mice (C57BL/6× SJL) at the National Transgenic Development Facility, using established techniques (35). The injected mouse eggs were reimplanted into pseudopregnant recipient females.

Analysis of DNA from Potential Transgenic Offspring

Genomic DNA was extracted from approximately 1 cm of tail tissue from 36 three week old offspring and tested for the presence of the transgene by polymerase chain reaction (PCR). The 5' primer was P6 in the dystrophin brain promoter (34), and the 3' primer represented the reverse complement of base pairs 2040–2062 from Kang et al. (9). PCR was carried out for 33 cycles (94° C. 1 minute, 50° C. 1 minute, 72° C. 3 minutes). The predicted 320 bp PCR product was detected in the DNA of 12 of 36 potential transgene founder mice. Genomic DNA was extracted from tail tissue by treating the tissue with 1% SDS, 550 ug/ml proteinase K at 55° C. overnight, and then adding sodium chloride to a final concentration of 1.5M, and the mixture was extracted with chloroform. DNA was precipitated from the aqueous phase with ethanol and resuspended overnight at 4° C. 200 ng of the DNA was used in the PCR reaction. Of these 12 positive mice, 10 survived for further analysis.

The copy number of the transgene in each founder line was then determined using Southern blot analysis. Microinjected DNA usually integrates into a genomic locus as multi-copy head-to-tail tandem arrays (35). 10 ug of DNA prepared as above was electrophoresed on 0.8% agarose gels and transferred to Hybond N (Amersham) membrane in the presence of 20× SSC (1× SSC=0.15M sodium chloride, 0.015M sodium citrate). Blots containing BamHI digested genomic DNA from the founder lines were hybridized with $^{32}P$ radiolabeled 4.65 kb DNA fragment or subfragments, prepared by the random hexanucleotide priming method (37). Blots were washed to a maximum stringency of 0.1× SSC at 65° C. with 0.1% SDS.

Figure 2:
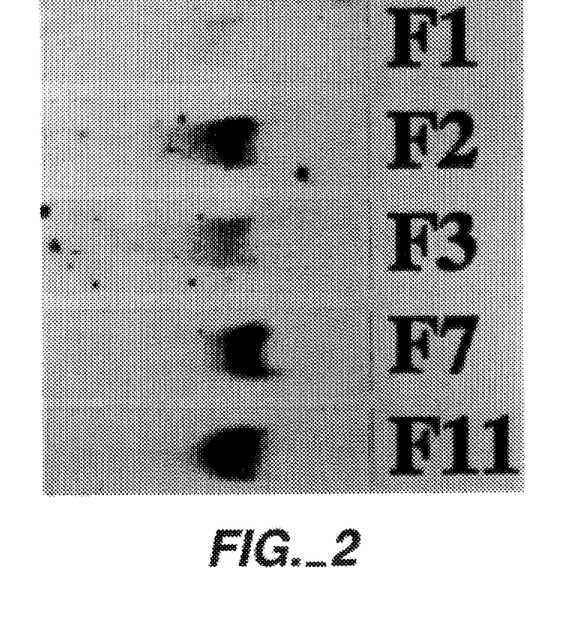
FIG. 2: Southern blot analysis of selected transgenic lines. All transgenes were detected within BamHI DNA bands greater than 20 kilobases in size. Lines 2, 7, and 11 had the greatest copy number, with more than 20 copies integrated.

Positively hybridizing bands exceeded 20 kb in all founder lines, indicating incorporation of the transgene into the mouse genome, since BamHI does not cleave within the transgene. Transgene copy number was estimated by comparing the intensity of a positively hybridizing internal transgene restriction fragment with that of an endogenous single copy band. Three founders (2, 7 and 11) carried more than 20 copies of the transgene, and one founder (4) appeared to carry only one copy. See FIG. 2. The remaining lines carried between three and ten copies each. Seven founder mice produced transgenic offspring in crosses with normal C57BL/6 mice, and Southern blot analysis of selected F1 and F2 progeny showed that the transgene was inherited with no observable rearrangements or changes in copy number.

Brain, skeletal muscle, heart and liver tissues were analyzed to determine the expression levels of the transgene in these tissues. Four month old F1 transgenic progeny from six founders and six month old founders that did not produce offspring were analyzed. RNA from these tissues was prepared from 100–500 mg of tissue by the guanidinium thiocyanate procedure with adaptations (38). The final step involved precipitation of the RNA with ½ volume of ethanol, which preferentially precipitates RNA but not DNA. 1 ug of RNA from each tissue was treated with DNAse I (0.3 U/ul in a volume of 12.1 ul) at 37° C. for 20 minutes to remove possible contaminating DNA. 3 ul of 0.1M MeHgOH was added to remove RNA secondary structure; 1.55 ul of 0.7M 2-mercaptoethanol was then added, after which cDNA was synthesized from each RNA sample in a 25 ul reverse transcription reaction (50 mM Tris [pH 8.2 at 42° C.], 50 mM KCl, 6 mM $MgCl_2$, 10 mM dithiothreitol, 1000 U/ml Promega Biotec RNAsin, 1 ug of 3' primer [identical to the 3' primer used in the tail DNA PCR reactions], 400 uM dNTPs, 350 U/ml Life Sciences AMV reverse transcriptase) that was incubated at 41.5° C. for 2 hours. The reaction was placed at 65° C. for 10 minutes to inactivate the reverse transcriptase. 1 uL of each cDNA reaction was used as template in a 50 uL PCR reaction mix (Perkin Elmer GeneAmp kit) containing 200 ng each of the primers (identical to the primers used for PCR analysis of tail DNA). The reactions were subjected to 40 cycles of PCR (same cycle as above), and then 40 uL of each reaction was electrophoresed on a 1% agarose gel in Tris-acetate-EDTA buffer and transferred to Hybond N (Amersham) in 20× SSC. The filter was then hybridized with an internal oligonucleotide probe that was $^{32}$P-label using T4 polynucleotide kinase (U.S. Biochemicals).

Figure 3:
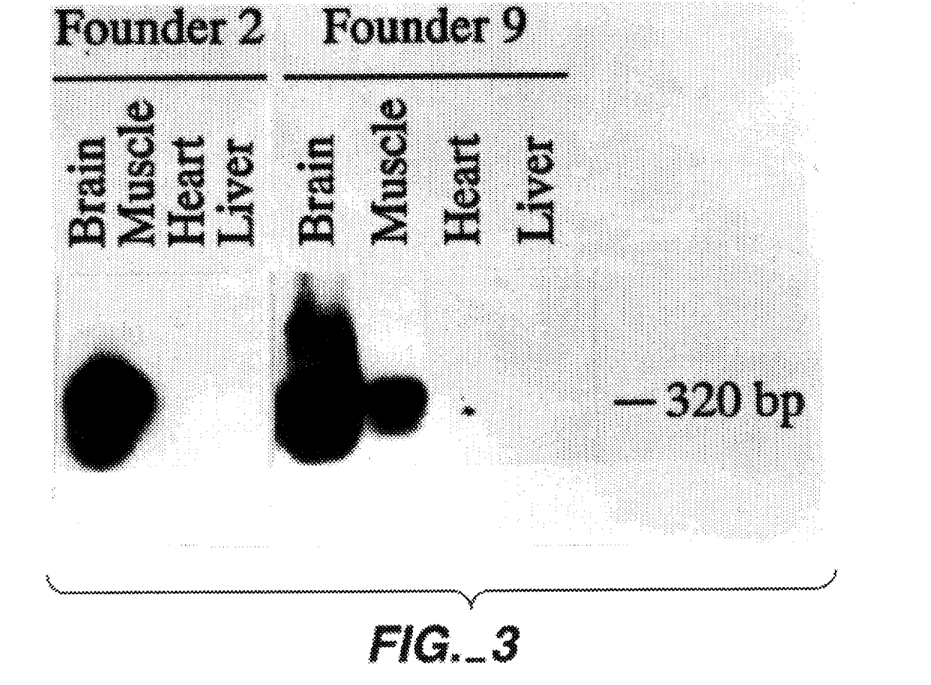
FIG. 3: Predominant brain expression of the βAPP-C104 transgene is revealed by RT-PCR. Hybridization of a radiolabeled interior oligonucleotide to a Southern blot of the RT-PCR amplification products from four RNAs in two of the transgenic lines is shown.
Figure 4A:
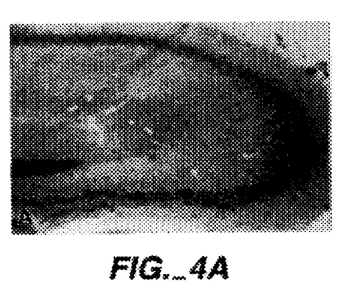
Figure 4B:
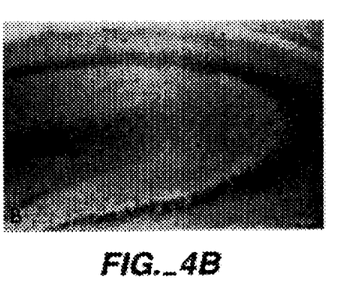
Figure 4C:
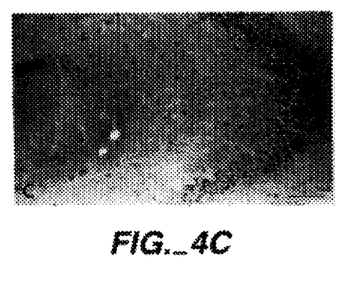
Figure 4D:
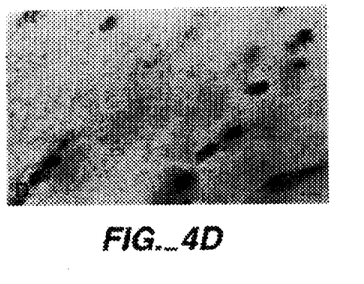
Figure 4E:
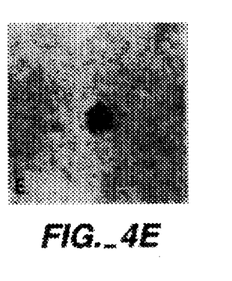

The predominant expression of the transgene occurred in the brain (FIG. 3). Ethidium bromide staining of the gel on which the RT-PCR products were electrophoresed showed a positively staining band of the expected size in the lanes containing the brain RT-PCR product of all founder lines. The most predominant bands included those from founders 2, 3, 4 and 7. At this level of sensitivity, no ethidium bromide-stained bands were visible in the lanes containing RT-PCR products of other tissues. Southern blot analysis of the RT-PCR products showed low levels of expression of the βAPP-C104 transgene in other tissues in some of the lines. However, expression of the transgene in brain exceeded its expression in any other tissue examined by at least a factor of ten in all transgenic animals.

Immunocytochemical Analysis of Brain Tissues

Two antisera were used for immunochemical analysis of the brains of the transgenic mice. The first, E1-42, was an affinity purified polyclonal antibody raised against a peptide representing the 42 amino acid β/A4 (amyloid) fragment. This antibody does not immunostain normal APP in the human brain, but is specific for pathological structures in Alzheimer's disease brain and (to a lesser extent) normal aged brain. These structures include amyloid cores in the neuritic plaques, as well as diffuse amyloid deposits that are not detectable by conventional histological stains for amyloid, such as thioflavin S.

14 F1 backcross progeny from 6 different founder lines (ages 3½ to 4 months) and founders only from 3 additional lines (aged 6 months) were analyzed. Also analyzed were 8 age matched C57BL/6 and SJL controls. The brains were either immersion fixed (in cases in which half the brain was used for RNA analysis) or were perfused with freshly prepared 4% paraformaldehyde buffered with 0.1M sodium phosphate, pH 7.2, and postfixed overnight at 4° C. before cryoprotection in 30% sucrose in 0.1M sodium phosphate, pH 7.2. The brains were frozen in a dry ice-acetone bathe maintained at −40° C., then processed immediately or stored at −70° C. The tissue was cut at 50 um intervals on a sliding microtime into ice-cold Tris-buffered saline (TBS; 50 mM Tris, pH 7.5, 300 mM NaCl).

The sections were pretreated with 1% $H_2O_2$ in TBS (100 mM Tris, pH 7.5, 145 mM NaCl) for 20 minutes, rinsed for 5 minutes in TBS and 15 minutes in TBS-A (TBS+0.1% Triton X-100), blocked for 30 minutes in TBS-B (TBS+2% BSA), and incubated overnight at room temperature in primary antibody diluted 1:750 in TBS-B. Sections were then rinsed for 15 minutes in TBS-A and 15 minutes in TBS-B, reacted with the secondary antibody (biotinylated goat anti-rabbit IgG, 1:250 in TBS-B according to the manufacturer's specifications for the Elite kit, Vector Labs, Burlingame, Calif.). Sections were then rinsed for 15 minutes in TBS-A and 15 minutes in TBS-B and reacted with HRP-conjugated avidin-biotin complex (as specified for the Elite kit, Vector Labs). After rinsing with 3× 5 minutes in TBS, the sections were then visualized using Vector Labs HRP substrate (diaminobenzidine) kit.

Figure 5A:
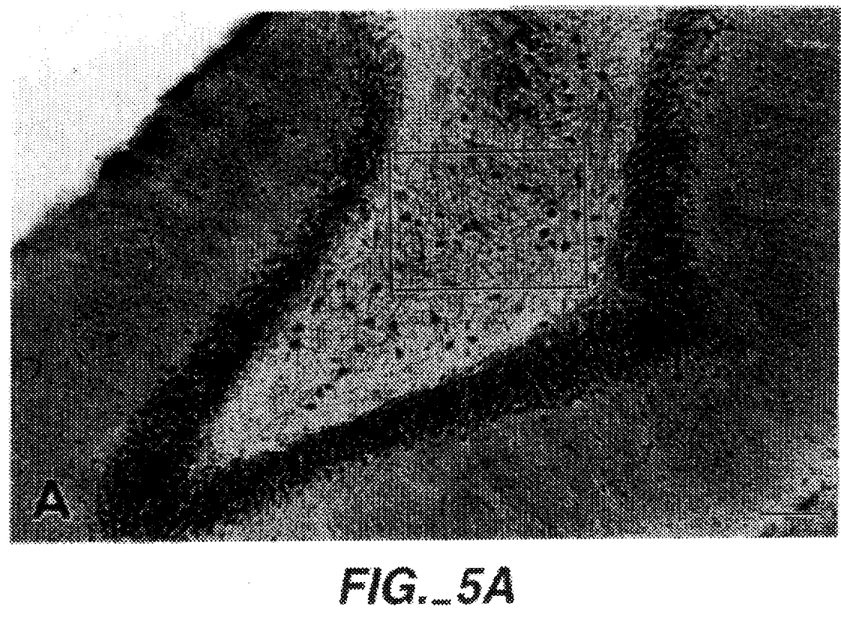
Figure 5B:
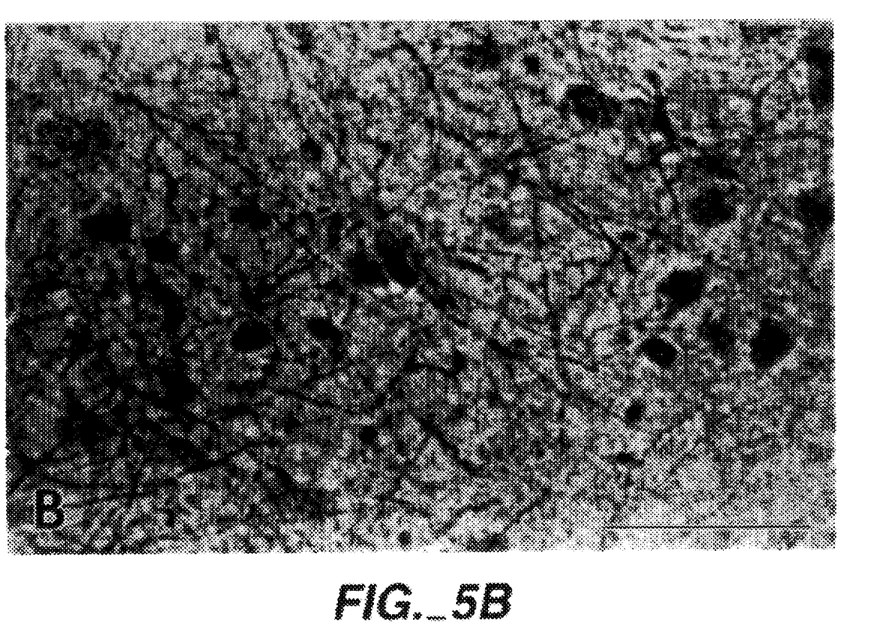

Immunostaining of control mouse brains showed that the E1-45 antibody recognized normal structures to some degree; very light homogeneous staining of cell bodies was evident in all nontransgenic mice (FIG. 4). In contrast, immunostaining of the brains of four-month old F1 transgenic mice from six lines, as well as the brains of the three six-month old founders, revealed intraneuronal amyloid deposition throughout the brain in all the transgenic mice. In the hippocampus, the E1-45 immunopositive cells were clearly visible in Ammon's horn and in the stratum oriens (FIG. 4). In most cases, the E1-45 immunoreactivity occurred as punctate deposits within neurons that had a rounded, compact appearance (FIG. 4). The intracellular accumulation of β/A4 (amyloid) was particularly prominent within the hilus (FIG. 5), and close examination of the E1-45 staining in this region showed that the immunoreactivity extended beyond the cell body, with punctate deposits visible in some processes (FIG. 5).

Figure 6A:
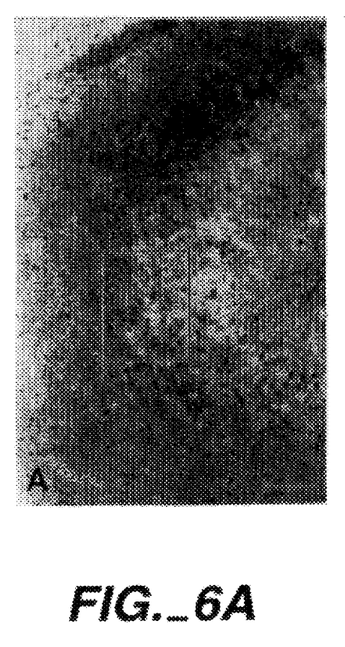
Figure 6B:
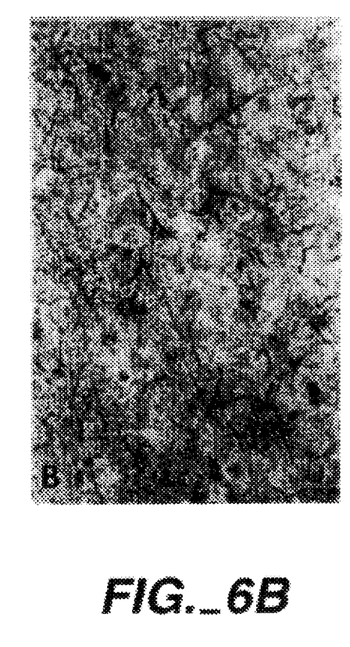
Figure 6C:
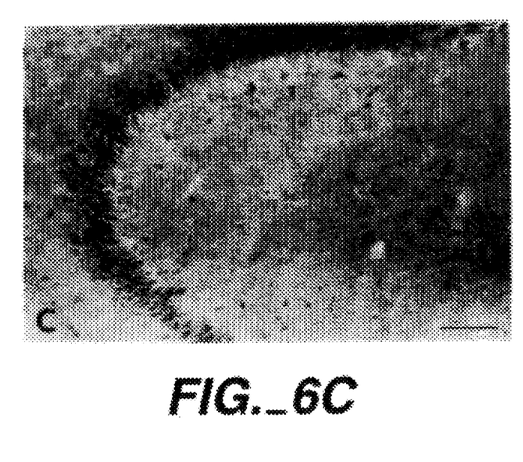
Figure 7A:
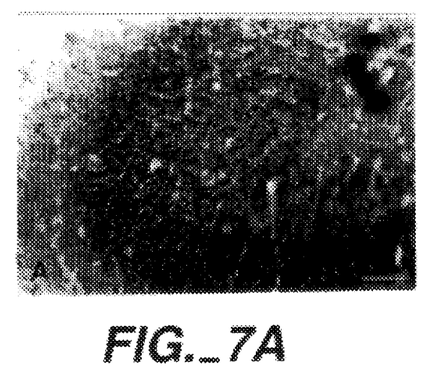
Figure 7B:
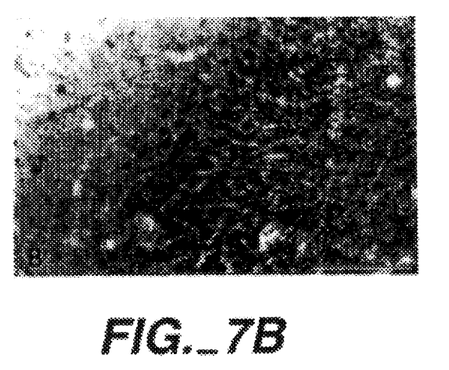
Figure 7C:
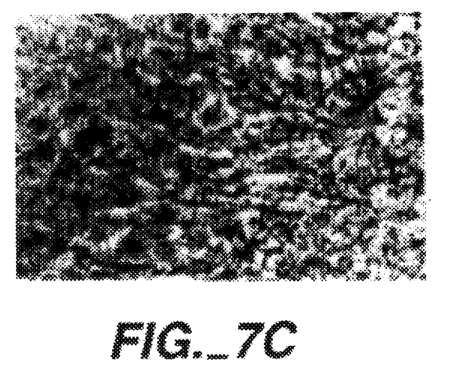
Figure 7D:
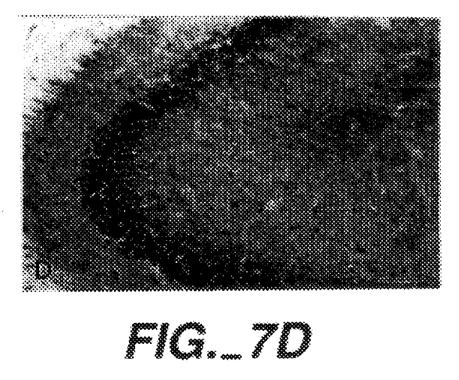
Figure 7E:
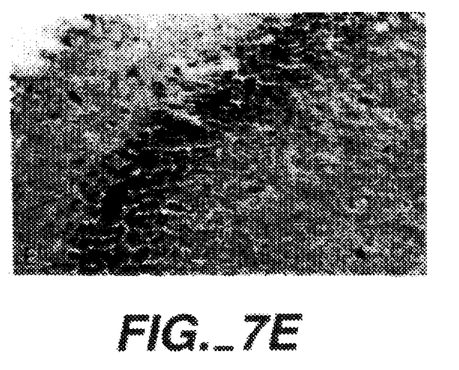
Figure 7F:
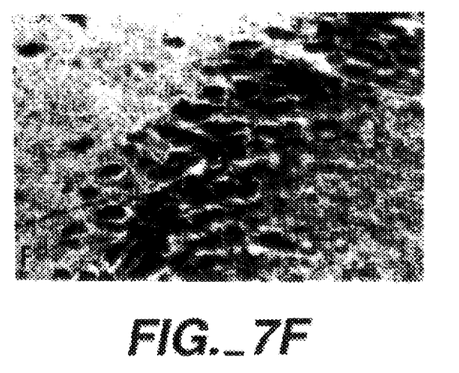
Figure 8A:
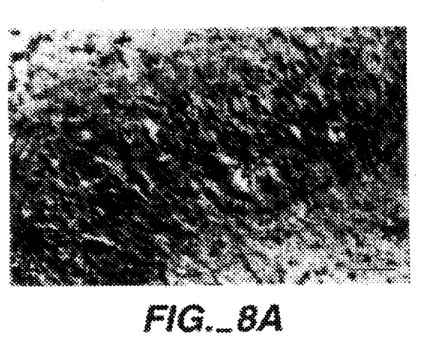
Figure 8B:
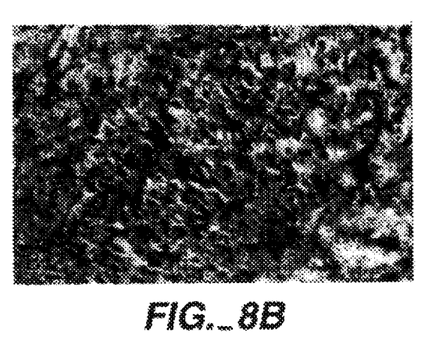
Figure 8C:
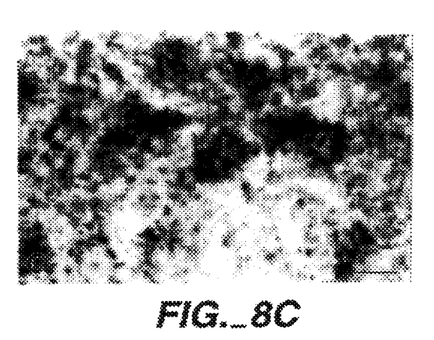
Figure 8D:
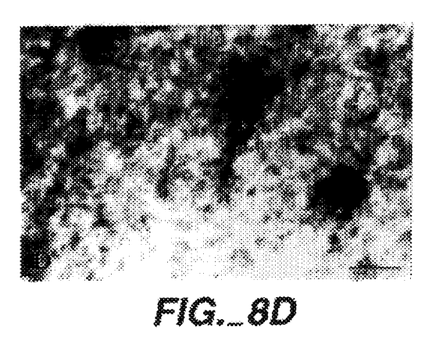

The emergence of E1-45 immunoreactivity in the neuropil may represent a later stage of amyloid deposition than that seen in the cell soma. This is suggested by the observation that punctate accumulations of β/A4 in short curly dystrophic-appearing fibers were dramatically apparent in the stratum radiatum of the CA2/3 region of the hippocampus of transgenic mice of the founder lines 2, 3 and 7 (FIG. 6). These three lines showed the highest transgene expression in the brain. In other transgenic founder lines, the punctate β/A4 immunoreactivity was confined to cell bodies in this region (FIG. 6).

The second antibody used in the immunohistochemistry analysis was F5, a polyclonal rabbit antibody raised against a peptide representing amino acids 687–695 of APP-695 (5). This antibody reacts with the carboxyterminus of normal APP, and also recognizes abnormal accumulations of APP in hippocampal neurons in Alzheimer's Disease. F5 immunohistochemistry was also carried out on human Alzheimer's Disease brains and age-matched controls.

Mouse brains were sectioned as for E1-45 treatment. The brain sections were then pretreated with 3% $H_2O_2$ in TBS (50 mM Tris pH 7.5, 300 mM NaCl) for 20 minutes and blocked for one hour in 0.3% Triton X-100, 20% goat serum in TBS. The sections were then washed 2× 15 minutes in TBS, and incubated for 40 hours at 4° C. in primary antibody diluted 1:1000 in 0.1% Triton X-100, 20% goat serum (TBST). Sections were then rinsed 2× 15 minutes in TBS and reacted with the secondary antibody (biotinylated goat anti-rabbit IgG, 1:250 in TBST according to Vector Lab's manufacturer's specifications). The sections were rinsed 2× 15 minutes in TBS, reacted with HRP-conjugated avidin-biotin complex (as specified by Vector Labs manufacturer's specifications) and rinsed 2× 15 minutes in TBS. The reaction was visualized using 0.05% diaminobenzidine (Sigma) plus 0.8% nickel chloride as a chromogen.

Human brain tissue of individuals with Alzheimer's Disease and age-matched controls was obtained in formalin, and was cyroprotected and cut as described for the mouse tissue except that the TBS used for the human tissue contained only 145 mM NaCl. The F5 immunocytochemistry was carried out as for the E1-45 mouse brain sections.

Staining of the mouse brain sections with F5 showed a striking change in the subcellular localization of the F5 epitope, that is particularly evident in the CA2/3 region of the hippocampus of the transgenic mice. Whereas control mice display homogeneous F5 staining predominantly of the neuronal somata in this region (FIG. 7), the F5 immunoreactivity in the transgenic mice took on a punctate appearance in the cell somata (FIG. 7) and extended markedly into the neuronal processes. Adjacent Nissl stained sections did not reveal detectable gross morphological abnormalities in the area of altered F5 staining, which suggests that the disorganization evident in the immunostained sections mainly involves the neuropil in transgenic mice of this age. This is the same F5 alterations in staining that are seen in human Alzheimer's Disease brains with age matched controls (see below). In mice from lines 2, 3 and 7, with the highest transgene expression in the brain, the cells of this region showed particularly dense reaction product in the neuropil, and the reactivity in the soma took the form of larger accumulations, as if the punctate vesicular immunoreactive material is fusing or aggregating (data not shown). The distribution of the F5 immunoreactivity in these cell is very similar to its distribution in CA1 neurons of Sommer's sector in human Alzheimer's Disease brains (9), and might be an early sign of developing pathology.

The same contrast in the F5 staining pattern was seen in the human brain sections (FIG. 8). The subcellular dislocation of the F5 epitope in Alzheimer's Disease was clear: whereas the F5 antibody displayed homogeneous cell soma staining in the pyramidal cell layer in the CA2/3 region of control hippocampus, (FIG. 8), it exhibited a punctate pattern of staining that extended to the neuropil in the same region of Alzheimer's Disease hippocampus (FIG. 8). The similarity in the appearance of the punctate cell body F5 immunoreactivity in transgenic animals and in Alzheimer's Disease individuals in this hippocampal sector was marked (FIG. 8).

Thioflavin S staining is commonly used in the analysis of Alzheimer's Disease brains, because it is a historic amyloid stain which highlights deposition of β/A4 in senile plaques and in the cerebral vasculature. Sections were incubated for 20 minutes in 1:1 100% ethanol:chloroform, and then rinsed 3× one minute in 95% ethanol, 3 minutes in 70% ethanol, 3 minutes in 50% ethanol, and 3 minutes in water. Sections were then incubated for four minutes in 1% thioflavin S (Sigma) in water and differentiated by rinsing in 80% ethanol. Sections were mounted onto chrom-alum subbed slides, covered and photographed.

Figure 9A:
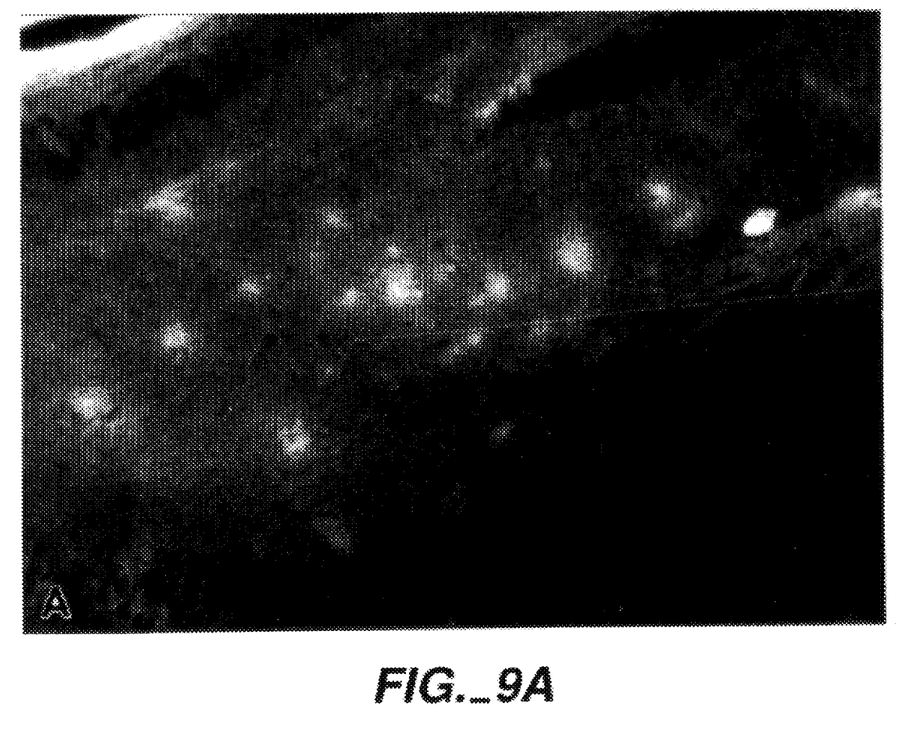
Figure 9B:
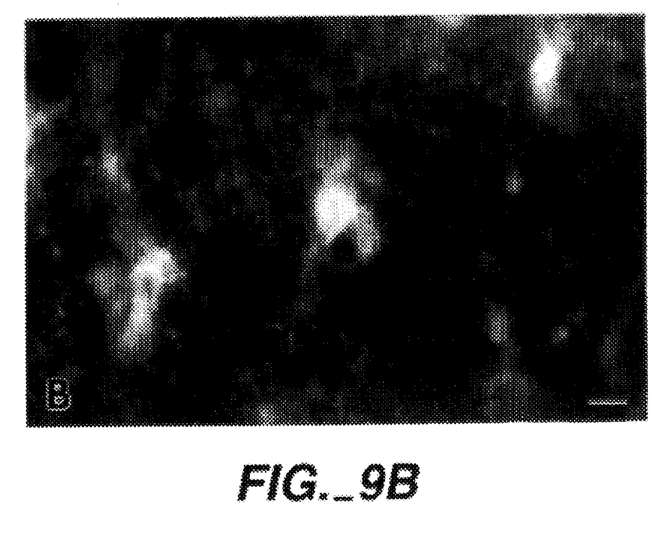

Thioflavin S staining showed no abnormal fluorescence of structures in the control mice, or in six of the transgenic mouse lines. However, the mice from line 2, 3, and 7, with the highest brain expression of the transgene, displayed prominent thioflavin S fluorescence around blood vessels (FIG. 9), which we also observed in human Alzheimer's Disease brains stained with thioflavin S.

BIBLIOGRAPHY (1): Cork et al. Animal Models of Degenerative Neurological Disease, in Animal Models: Assessing the Scope of Their Use in Biomedical Research, pp 241–269. 1987 Alan R. Liss, Inc.

(2): Wolozin et al. Science 232, 648 (1986).

(3): Ksiezak-Reding et al., J. Biol. Chem. 263, 7943 (1988).

(4): Kowall et al., Ann. Neurol. 22, 639 (1987).

(5): Benowitz et al., Exptl. Neuro. 106, 237 (1989).

(6): Roch et al. (1966) Nature (London) 209, 109.

(7): Glenner, (1983) Arch. Pathol. Lab. Med 107, 281.

(8): Dyrks et al. EMBO J. 7, 949 (1988).

(9): Kang et al., Nature 325, 733 (1987).

(10): Goldgaber et al., Science 235, 877 (1987).

(11): Tanzi et al., Science 235, 880 (1987).

(12): Robakis et al., Proc. Natl. Acad. Sci. USA 84, 4190 (1987).

(13): Tanzi et al., Nature 331, 528 (1988).

(14): Ponte et al., Nature 331, 525 (1988).

(15): Kitaguchi et al., Nature 331, 530 (1988).

(16): Golde et al., Neuron 4, 253 (1990).

(17): Glenner et al. Biochem. Biophys. Res. Commun. 120, 885 (1984)

(18): Glenner et al. Biochem. Biophys. Res. Commun. 122, 1131 (1984)

(19): Masters et al. Proc. Natl. Acad. Sci. USA 82, 4245 (1985)

(20): Shivers et al. EMBO J. 7, 1365 (1988)

(21): Podlisney et al. A. J. Pathol., in press (1991)

(22): Manning et al. Mol. Brain Res. 3, 293 (1988)

(23): Esch et al. Science 248, 1122 (1990)

(24): Yankner et al. Science 245, 417 (1989).

(25): Castano et al. Biochem. Biophys. Res. Commun. 141, 782 (1986)

(26): Gorevic et al. Biochem. Biophys. Res. Commun. 147, 854 (1987)

(27): Kirschner et al. Proc. Natl. Acad. Sci. USA 84, 6953 (1987)

(28): Wolf et al. EMBO J. 9, 2079 (1990).

(29): Maruyama et al. Nature 347, 566 (1990).

(30): Neve et al. Neuron 5, 329 (1990).

(31): Dayan Acta Neuropathol (Berl) 16, 85 (1970)

(32): Katzman et al. Ann. Neurol. 23, 138 (1988)

(33): Kemper, in Clinical Neurology of Aging. Albert M. L. ed. New York, Oxford University Press, 9–52 (1984)

(34): Boyce et al. Proc. Natl. Acad. Sci. USA 88, 1276 (1991)

(35): Palmiter et al. Cell 41, 343 (1985)

(36): Gorman et al. Science 221, 877 (1987)

(37): Feinberg et al. Anal. Biochem. 132, 6 (1983)

(38): Neve et al. Mol. Brain Res. 1, 271 (1986)

What is claimed is:

1. A transgenic mouse whose somatic and germ cells contain a transgene encoding an about 100 amino acid neurotoxic C-terminal fragment of the β-amyloid precursor protein, wherein said transgene is operably linked to a brain tissue promoter, and wherein expression of said transgene results in the formation of punctate deposits in neuronal processes of the mouse's brain.

2. The mouse according to claim 1, wherein said transgene encodes APP-C104.

3. The mouse according to claim 1, wherein said transgene encodes the human polypeptide fragment APP-C104.

4. The mouse according to claim 1, wherein said promoter is the dystrophin neural promoter.

5. A progeny mouse of the mouse according to claim 1, wherein the somatic and germ cells of said progeny mouse contain a transgene encoding an about 100 amino acid neurotoxic C-terminal fragment of the 13-amyloid precursor protein, wherein said transgene is operably linked to a brain tissue promoter, and wherein the expression of said transgene results in the formation of punctuate deposits in neuronal processes of said progeny mouse's brain.

6. A method of determining the effect of compounds on the development of punctate deposits in neuronal processes of the mouse's brain, wherein said compounds are administered to the mouse of claims 1 or 2, and the effect of said compounds on the development of said deposits monitored.

7. The method according to claim 6, wherein the compounds are selected from the group consisting of hormones, polypeptides and nucleotides.

8. The method according to claim 6, wherein said monitoring comprises measuring the inhibitory effect of said compounds on the development of said deposit.

* * * * *